United States Patent
Muratake et al.

(10) Patent No.: US 9,353,134 B2
(45) Date of Patent: *May 31, 2016

(54) SILICON-CONTAINING CARBOXYLIC ACID DERIVATIVE

(71) Applicant: KEMPHYS LTD., Tokyo (JP)

(72) Inventors: Hideaki Muratake, Tokyo (JP); Ai Ito, Tokyo (JP); Koichi Shudo, Tokyo (JP)

(73) Assignee: KEMPHYS LTD., Tokyo (JP)

( * ) Notice: Subject to any disclaimer, the term of this patent is extended or adjusted under 35 U.S.C. 154(b) by 0 days.

This patent is subject to a terminal disclaimer.

(21) Appl. No.: 14/435,621

(22) PCT Filed: Oct. 17, 2013

(86) PCT No.: PCT/JP2013/078121
§ 371 (c)(1),
(2) Date: Apr. 14, 2015

(87) PCT Pub. No.: WO2014/061714
PCT Pub. Date: Apr. 24, 2014

(65) Prior Publication Data
US 2015/0232487 A1    Aug. 20, 2015

Related U.S. Application Data

(60) Provisional application No. 61/715,399, filed on Oct. 18, 2012.

(51) Int. Cl.
C07F 7/08        (2006.01)
C07F 7/10        (2006.01)

(52) U.S. Cl.
CPC ................... *C07F 7/0818* (2013.01)

(58) Field of Classification Search
CPC ............................. C07C 7/0818; C07C 7/10
USPC .................................................. 556/418
See application file for complete search history.

(56) References Cited

U.S. PATENT DOCUMENTS

| | | | | |
|---|---|---|---|---|
| 2,628,245 A | * | 2/1953 | Speier, Jr. ............. | C07F 7/0818 556/437 |
| 5,563,175 A | * | 10/1996 | Silverman ............. | A61K 31/197 514/561 |
| 5,629,447 A | * | 5/1997 | Huckabee ............. | C07C 211/27 562/553 |
| 5,840,956 A | * | 11/1998 | Grote .................... | C07C 227/10 558/441 |

FOREIGN PATENT DOCUMENTS

| | | |
|---|---|---|
| GB | 688178 | 2/1953 |
| GB | 2 397 576 | 7/2004 |
| WO | 2012/144551 | 10/2012 |

OTHER PUBLICATIONS

Daiβ et al., "β-Carbonylsilanes with a Silacyclohexane Skeleton and Additional C-functionalized Organyl Groups at the Silicon Atom: Synthesis, Reactivity, and NMR-spectroscopic Characterization", *Journal of Organometallic Chemistry*, vol. 690, pp. 678-684, 2005.
Muratake et al., "(R)- and (S)-4Amino-3-(trimethylsilyl)methylbutanoic Acids Ameliorate Neuropathic Pain Without Central Nervous System-Related Side Effects", *Bioorganic & Medicinal Chemisty Letters*, vol. 22, pp. 7602-7604, published online Oct. 10, 2012.
Kheifits et al., "Perfumes from alkylphenols. I. Synthesis of perfumes from dimethylphenyl-p-cresol", *Zhurnal Obshchei Khimii*, vol. 30, pp. 1367-1373, 1960.
Fukazawa et al., "Silagaba as Novel Agents for Neuropathic Pain Without Upper-CNS Side Effects", *Pain Research*, vol. 28, No. 2, p. 100, 2013.
International Search Report and Written Opinion for PCT/JP2013/078121, mailed Dec. 17, 2013.
International Preliminary Report on Patentability for PCT/JP2013/078121, mailed Apr. 30, 2015, along with an English language translation thereof.

* cited by examiner

*Primary Examiner* — Sikarl Witherspoon
(74) *Attorney, Agent, or Firm* — Greenblum & Bernstein, P.L.C.

(57) ABSTRACT

A compound represented by the formula (I) [at least one of $R^1$, $R^2$, and $R^3$ represents a cyclic alkyl group, the remaining represents a linear or branched alkyl group; n represents 0 or 1; $R^4$ represents an amino group or $-(CX_2)_m-COOH$ (m represents 0 to 3, and X represents hydrogen atom); and $R^5$ represents $-(CY_2)_p-COOR^6$ (p represents 0 to 3, Y represents hydrogen atom, and $R^6$ represents hydrogen atom or an alkyl group)], or a salt thereof.

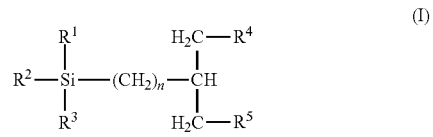

(I)

3 Claims, No Drawings

SILICON-CONTAINING CARBOXYLIC ACID DERIVATIVE

CLAIM FOR PRIORITY

This application is a U.S. National Stage of PCT/JP2013/078121 filed on Oct. 17, 2013, and claims the priority benefit of U.S. provisional application 61/715,399, filed Oct. 18, 2012, the contents of which is expressly incorporated by reference herein in their entireties.

TECHNICAL FIELD

The present invention relates to a silicon-containing carboxylic acid derivative.

BACKGROUND ART

Carboxyl group is one of important functional groups in pharmaceutical compounds, and is widely used in combination with various functional groups, such as amino group, hydroxyl group, and a halogen atom. For example, gabapentin (2-[1-(aminomethyl)cyclohexyl]acetic acid) used an antiepileptic, and pregabalin ((S)-3-(aminomethyl)-5-methylhexanoic acid) used for peripheral neuropathic pains (postherpetic neuralgia and the like) are examples of medicaments having carboxyl group and amino group in combination.

There have been proposed pharmaceutical compounds consisting of a carboxylic acid derivative in which a carbon atom is replaced with a silicon atom. For example, a β-carbonylsilane compound having a silicon atom as a ring-constituting atom in a ring system such as 6-membered ring has been proposed as an analogue of gabapentin (GB 2,397,576A), and it is taught that this compound can be used as a pharmaceutical compound (Journal of Organometallic Chemistry, 690, pp. 678-684, 2005, with reference to the method for preparation of this compound). However, any compounds corresponding to pregabalin of which carbon atom in the fundamental structure thereof is replaced with a silicon atom are not known.

PRIOR ART REFERENCES

Patent Document

Patent document 1: GB 2,397,576A

Non-Patent Document

Non-patent document 1: Journal of Organometallic Chemistry, 690, pp. 678-684, 2005

SUMMARY OF THE INVENTION

Object to be Achieved by the Invention

An object of the present invention is to provide a novel silicon-containing carboxylic acid derivative useful as an active ingredient of medicaments, and the like.

Means for Achieving the Object

The inventors of the present invention conducted various researches to provide a novel silicon-containing carboxylic acid derivative, and as a result, they found that compounds represented by the following general formula (I) were useful as active ingredients of medicaments and the like, and accomplished the present invention.

The present invention thus provides a compound represented by the following general formula (I):

[Formula 1]

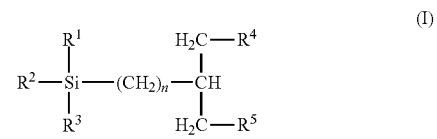

[wherein, at least one of $R^1$, $R^2$, and $R^3$ represents a cyclic alkyl group, the remaining represents a linear or branched alkyl group; n represents 0 or 1; $R^4$ represents an amino group (this amino group may have a substituent) or $-(CX_2)_m-$COOH (m represents an integer of 0 to 3, and X represents hydrogen atom or deuterium atom); $R^5$ represents $-(CY_2)_p-COOR^6$ (p represents an integer of 0 to 3, Y represents hydrogen atom or deuterium atom, and $R^6$ represents hydrogen atom or an alkyl group (this alkyl group may have a substituent))], or a salt thereof.

According to preferred embodiments of the aforementioned invention, there are provided the aforementioned compound or a salt thereof, wherein $R^1$ is cyclopropyl group, $R^2$, and $R^3$ are methyl groups, n is 0 or 1, $R^4$ is an amino group, a monoalkylamino group, or an acylamino group, and $R^5$ is $-(CH_2)_p-COOR^6$ (p represents an integer of 0 to 3, and $R^6$ is hydrogen atom or an alkyl group), and the aforementioned compound or a salt thereof, wherein $R^1$ is cyclopropyl group, $R^2$, and $R^3$ are methyl groups, n is 1, $R^4$ is an amino group, and $R^5$ is $-(CH_2)_p-COOR^6$ (p represents an integer of 0 to 3, and $R^6$ is hydrogen atom or an alkyl group).

As another aspect, the present invention provides a medicament containing a compound represented by the aforementioned general formula (I) or a physiologically acceptable salt thereof as an active ingredient.

The present invention also provides use of a compound represented by the aforementioned general formula (I) or a physiologically acceptable salt thereof for manufacture of the aforementioned medicament; and a method for prophylactic and/or therapeutic treatment of a disease of a mammal including human, which comprises the step of administering a prophylactically and/or therapeutically effective amount of a compound represented by the aforementioned general formula (I) or a physiologically acceptable salt thereof to a mammal including human.

Effect of the Invention

The compounds represented by the aforementioned general formula (I) and salts thereof provided by the present invention can be used as, for example, an active ingredient of medicaments. They have superior stability in vivo, and are useful as an active ingredient of medicaments with a sustained metabolic rate.

Modes for Carrying out the Invention

At least one of $R^1$, $R^2$, and $R^3$ represents a cyclic alkyl group, and the remaining represents a linear or branched alkyl group. As the cyclic alkyl group, a cyclic alkyl group having about 3- to 10-membered ring, preferably about 3- to 6-membered ring, can be used, and cyclopropyl group, cyclobutyl group, cyclopentyl group, and the like can be particularly preferably used. On the ring of the cyclic alkyl group, one or two or more linear or branched alkyl groups may substitute. As such a linear or branched alkyl group, an alkyl group having about 1 to 6 carbon atoms, such as methyl group and ethyl group, can be used. It is preferred that one of $R^1$, $R^2$, and $R^3$ is a cyclic alkyl group, and as the cyclic alkyl group, cyclopropyl group, cyclobutyl group, or cyclopentyl group is preferred.

$R^1$, $R^2$, and $R^3$ that do not represent a cyclic alkyl group independently represent a linear or branched alkyl group. Although number of carbon atom of this alkyl group is not particularly limited, it is, for example, about 1 to 18, preferably about 1 to 12, more preferably about 1 to 6, particularly preferably about 1 to 4. This alkyl group may have one or two or more substituents. When they have two or more substituents, they may be the same or different. Substitution position of the substituent is not particularly limited, and the alky group may have one or more substituents at arbitrary position(s). Examples of the substituent include, for example, a halogen atom (fluorine atom, chlorine atom, bromine atom, or iodine atom), hydroxyl group, oxo group, carboxyl group, an alkoxycarbonyl group, an acyl group, amino group, an alkyl group, an alkenyl group, an alkynyl group, an alkoxyl group, an aryl group, an aralkyl group, and the like, but are not limited to these examples. These substituents may be further substituted with another substituent. Examples of the substituent of such a case include, for example, a fluoroalkyl group, fluoroacetyl group, methoxybenzyl group, and the like, but are not limited to these examples.

Symbol n represents 0 or 1. When n is 0, it is meant that methylene group does not exist. It is preferred that n is 1

$R^4$ represent an amino group or $-(CX_2)_m-COOH$. The amino group represented by $R^4$ may have one or two substituents. As the substituent, for example, an alkyl group, an alkenyl group, an alkynyl group, an aryl group, an acyl group (for example, an alkanoyl group such as acetyl group, an aroyl group such as benzoyl group, and the like), and the like can be used, but the substituent is not limited to these examples. Further, examples of the amino group substituted with an acyl group include an acylamino group formed by amino group and carboxyl group of an amino acid bound with an amide bond (for example, see, International Patent Publication WO02/100344, and the like), a carbamate group (for example, one formed by binding (2-methyl-1-oxopropyloxy) ethoxycarbonyl group with amino group), and the like, but are not limited to these examples. Modification of the amino group with these acyl groups is useful for use as a prodrug, sustained release preparation, or the like. The amino group represented by $R^4$ preferably does not have a substituent, or has one alkyl group or acyl group. When the amino group has one alkyl group, number of carbon atoms of the alkyl group is about 1 to 6.

In the group represented as $-(CX_2)_m-COOH$ as $R^4$, m represents an integer of 0 to 3, and m is preferably 1 or 2, more preferably 1. X represents hydrogen atom or deuterium atom. When X is deuterium atom, it is meant that substitution ratio of deuterium (ratio of hydrogen atoms replaced with deuterium atoms) is at least 50%, preferably 70% or higher, more preferably 80% or higher, particularly preferably 90% or higher, most preferably 95% or higher, and it is not necessary that hydrogen atoms are completely replaced with deuterium atoms. Therefore, the expression that X is deuterium atom should be construed to include a case that a part of X consists of hydrogen atoms. As $R^4$, an amino group is preferred, and the amino group is preferably unsubstituted amino group or a monoalkylamino group.

In the group represented as $-(CY_2)p-COOR^6$ as $R^5$, p represents an integer of 0 to 3, and p is preferably 1 or 2, more preferably 1. Symbol Y represents hydrogen atom or deuterium atom, and the explanation for X is similarly applied to Y. $R^6$ represents hydrogen atom or an alkyl group, and the alkyl group represented by $R^6$ may have a substituent. Examples of the substituent include, for example, a halogen atom (fluorine atom, chlorine atom, bromine atom, or iodine atom), hydroxyl group, oxo group, carboxyl group, an alkoxycarbonyl group, an acyl group, amino group, an alkyl group, an alkenyl group, an alkynyl group, an alkoxyl group, an aryl group, an aralkyl group, and the like, but are not limited to these examples. These substituents may be further substituted with another substituent. Examples of the substituent of such a case include, for example, a fluoroalkyl group, methoxymethyl group, ethoxymethyl group, and the like, but are not limited to these examples.

Specific examples of $R^6$ as the alkyl group which may be substituted, and forms an ester include, for example, methyl group, ethyl group, propyl group, isopropyl group, butyl group, isobutyl group, t-butyl group, benzyl group, acetoxymethyl group, 1-(acetoxy)ethyl group, propionyloxymethyl group, 1-(propionyloxy)ethyl group, butyryloxymethyl group, 1-(butyryloxy)ethyl group, isobutyryloxymethyl group, 1-(isobutyryloxy)ethyl group, valeryloxymethyl group, 1-(valeryloxy)ethyl group, isovaleryloxymethyl group, 1-(isovaleryloxy)ethyl group, pivaloyloxymethyl group, 1-(pivaloyloxy)ethyl group, methoxycarbonyloxymethyl group, 1-(methoxycarbonyloxy) ethyl group, ethoxycarbonyloxymethyl group, 1-(ethoxycarbonyloxy)ethyl group, propoxycarbonyloxymethyl group, 1-(propoxycarbonyloxy)ethyl group, isopropoxycarbonyloxymethyl group, 1-(isopropoxycarbonyloxy) ethyl group, butoxycarbonyloxymethyl group, 1-(buthoxycarbonyloxy)ethyl group, isobutoxycarbonyloxymethyl group, 1-(isobuthoxycarbonyloxy)ethyl group, t-buthoxycarbonyloxymethyl group, 1-(t-buthoxycarbonyloxy)ethyl group, cyclopentanecarbonyloxymethyl group, 1-(cyclopentanecarbonyloxy)ethyl group, cyclohexanecarbonyloxymethyl group, 1-(cyclohexanecarbonyloxy)ethyl group, cyclopenthyloxycarbonyloxymethyl group, 1-(cyclopenthyloxycarbonyloxy)ethyl group, cyclohexyloxycarbonyloxymethyl group, 1-(cyclohexyloxycarbonyloxy)ethyl group, benzoyloxymethyl group, 1-(benzoyloxy)ethyl group, phenoxycarbonyloxymethyl group, 1-(phenoxycarbonyloxy)ethyl group, (5-methyl-2-oxo-1,3-dioxolen-4-yl)methyl group, 2-trimethylsilylethyl group, and the like, but are not limited to these examples.

The compounds represented by the general formula (I) may form an acid addition salt or a base addition salt. Examples of the acid addition salt include, for example, mineral acid salts such as hydrochloride, sulfate, and nitrate, organic acid salts such as p-toluenesulfonate, oxalate, and malate, and the like, but are not limited to these examples. Examples of the base addition salt include, for example, metal salts such as sodium salt, potassium salt, magnesium salt, and calcium salt, ammonium salts, organic amine salts such as triethylamine salt and ethanolamine salt, and the like, but are not limited to these examples. Among these salts, physiologically acceptable salts are preferred, when the compounds of the present invention are used as an active ingredient of medicaments.

Further, the compounds represented by the general formula (I) may have one or two or more asymmetric carbons depending on the type of substituent, and arbitrary optical isomers based on these asymmetric carbons, arbitrary mixtures of optical isomers, racemates, diastereoisomers based on two or more asymmetric carbons, arbitrary mixtures of diastereoisomers, and the like are all encompassed within the scope of the present invention. When the compounds represented by the general formula (I) contain a double bond, geometrical isomers thereof may exist, and Z-isomers and E-isomers in pure forms, as well as mixture of them at arbitrary ratios are also encompassed within the scope of the present invention. Furthermore, arbitrary hydrates or solvates of the free compounds and salts thereof are also encompassed within the scope of the present invention.

The compounds of the present invention represented by the general formula (I) can be synthesized by the methods specifically described in the examples of this specification. Since synthesis methods of β-carbonylsilanes, having a silicon atom instead of a carbon atom, have been reported (for example, GB 2,397,576A and Journal of Organometallic Chemistry, 690, pp. 678-684, 2005), those skilled in the art can easily prepare arbitrary compounds of the general formula (I) by referring to the synthetic methods specifically described in the examples of this specification together with the aforementioned publications. Further, as for the synthetic method of the compounds having an amino acid and carboxyl group, for example, the synthesis methods of pregabalin and analogues thereof (U.S. Pat. Nos. 5,563,175, 5,840,956, 5,637,767, 5,629,447, 5,616,793, 5,563,175, and the like) can also be referred to.

Although the use of the compounds of the present invention represented by the general formula (I) is not particularly limited, they can be used as, for example, active ingredients of medicaments. Examples of use of the medicaments include, for example, prophylactic and/or therapeutic treatment of epilepsy, pains, inflammations, gastrointestinal disorders, insomnia, mental disorders, diabetic peripheral nerve disorders, and the like, but are not limited to these examples. Among the compounds of the present invention, the compounds having an amino acid and carboxyl group are expected to have the same pharmacological actions as those of, for example, pregabalin or gabapentin, and therefore they can be used for the specific uses described in, for example, International Patent Publication WO2010/017498, paragraph [0003] and the like. The entire disclosure of the aforementioned patent document is incorporated into the disclosure of this specification by reference. For example, as for binding to a gabapentin receptor, gabapentin receptors can be prepared from the brain of Wister rat according to the method of Suman-Chauhan et al. (Eur. J. Pharmacol, 244 (3), pp. 293-301, 1993), and binding of a test compound (1 µM) to the gabapentin receptors can be investigated on the basis of inhibition of binding of gabapentin in the presence of 0.02 µM [$^3$H] gabapentin. As for analgesic action, a test compound can be orally administered to a rat Chung model, and the analgesic action can be measured by using a pain threshold value for mechanical stimulation. However, the methods for confirming the pharmacological actions of the compounds of the present invention are not limited to these methods.

When a compound of the present invention represented by the general formula (I) or a physiologically acceptable salt thereof is used as a medicament, the compound, a physiologically acceptable salt thereof, or a hydrate or solvate thereof per se may be administered to a mammal including human, but it can be preferably administered as a pharmaceutical composition for oral or parenteral administration that can be prepared by a method well known to those skilled in the art. Examples of the pharmaceutical composition suitable for oral administration include, for example, tablets, capsules, powders, subtilized granules, granules, solutions, syrups, and the like, and examples of the pharmaceutical composition suitable for parenteral administration include, for example, injections, fusion drips, suppositories, inhalants, eye drops, nose drops, ointments, creams, patches, transdermal preparations, transmucosal preparations, and the like.

For the preparation of these pharmaceutical compositions, one or two or more kinds of pharmaceutical additives available for those skilled in the art can be used. Examples of the pharmaceutical additives include, for example, excipients, disintegrating agents or disintegrating aids, binders, lubricants, coating agents, dyes, diluents, bases, dissolving agents or dissolving aids, isotonic agents, pH modifiers, stabilizers, propellants, tackifiers, and the like. These additives can be appropriately chosen by those skilled in the art according to the form of the pharmaceutical composition, and two or more kinds of them may be used in combination. Dose of the medicament is not particularly limited, and can be appropriately determined depending on various factors which should usually be taken into consideration, such as weight and age of patients, type and symptoms of disease, and administration route.

For example, in the case of oral administration, the compound or a salt thereof can be used in an amount in the range of about 0.001 to 10,000 mg per day for adults.

EXAMPLES

Hereafter, the present invention will be still more specifically explained with reference to examples. However, the scope of the present invention is not limited to the following examples.

Example 1

Preparation of chloromethyl(cyclopropyl)dimethylsilane

A suspension of metal magnesium (2.19 g, 91.3 mg atom) in tetrahydrofuran (THF, 60 ml) was added with iodine (small pellet), and the mixture was added dropwise with bromocyclopropane (7.3 ml, 91.7 mmol) under an argon atmosphere with occasional ice cooling. After-dissolution of magnesium, the reaction vessel was cooled on ice, and the reaction mixture was added dropwise with a solution of chloro(chloromethyl)dimethylsilane (10.0 ml, 75.9 mmol) in THF (15 ml) over about 10 minutes. The vessel used for the addition was washed with THF (5 ml), and the washing solution was combined with the reaction mixture. The reaction mixture was stirred for 30 minutes under ice cooling and for further 16 hours at room temperature, then poured onto ammonium chloride/ice, and then extracted with diethyl ether. The organic layer was washed with saturated brine, and then distilled at ordinary pressure to obtain chloromethyl(cyclopropyl)dimethylsilane (7.69 g, 68%) mentioned in the title as colorless oil.

Bp: 151 to 154° C./760 mmHg $^1$H-NMR (CDCl$_3$) δ: −0.34 (1H, dddd, J=9.5, 9.5, 7, 7 Hz), 0.03 (6H, s), 0.23-0.29 (2H, m), 0.57-0.66 (2H, s), 2.80 (2H, s)

Example 2

Preparation of ethyl 3-cyclopropyl(dimethyl)silyl[-2-cyanopropionate

[Formula 2]

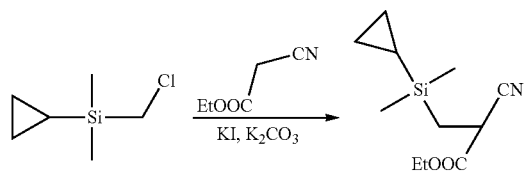

Chloromethyl(cyclopropyl)dimethylsilane (7.68 g, 51.7 mmol) was condensed with ethyl cyanoacetate in the same manner as that of Example 1, and the reaction mixture was treated in a conventional manner, and then distilled under reduced pressure to obtain ethyl 3-cyclopropyl(dimethyl)silyl-2-cyanopropionate (8.34 g, 72%) mentioned in the title as colorless oil.

Bp: 130 to 135° C./8 mmHg $^1$H-NMR (CDCl$_3$) δ: −0.37 (1H, dddd, J=9.5, 9.5, 7, 7 Hz), 0.020 (3H, s), 0.023 (3H, s), 0.21-0.27 (2H, m), 0.57-0.68 (2H, m), 1.26 (1H, dd, J=14.5, 9 Hz), 1.32 (1H, dd, J=14.5, 7 Hz), 1.33 (3H, t, J=7 Hz), 3.55 (1H, dd, J=9, 7 Hz), 4.20-4.31 (2H, m)

Example 3

Preparation of ethyl 4-cyclopropyl(dimethyl)silyl-3-cyanobutanoate

[Formula 3]

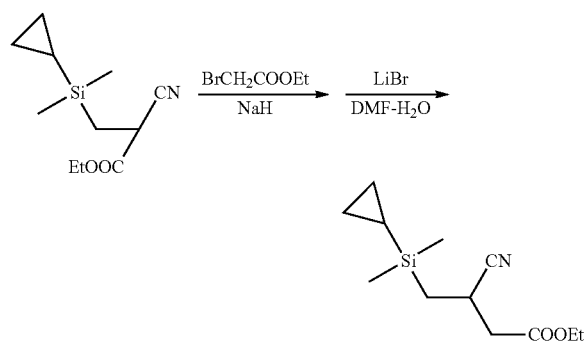

Ethyl 3-cyclopropyl(dimethyl)silyl-2-cyanopropionate (8.34 g, 37.1 mmol) was condensed with ethyl bromoacetate in the same manner as that of Example 1, the reaction mixture was treated in a conventional manner, and then the obtained reaction mixture (11.86 g) was treated with lithium bromide monohydrate (4.67 g, 44.5 mmol) in dimethylformamide. The reaction mixture was treated in a conventional manner, and then distilled under reduced pressure to obtain ethyl 4-cyclopropyl(dimethyl)sily-3-cyanobutanoate (7.71 g, total 87%) mentioned in the title as colorless oil.

Bp: 144 to 147° C./8 mmHg $^1$H-NMR (CDCl$_3$) δ: −0.36 (1H, dddd, J=9.5, 9.5, 7, 7 Hz), 0.02 (6H, s), 0.18-0.29 (2H, m), 0.57-0.69 (2H, m), 0.90 (1H, dd, J=14.5, 5.5 Hz), 1.05 (1H, dd, J=14.5, 10.5 Hz), 1.29 (3H, t, J=7 Hz), 2.60 (1H, dd, J=16.5, 7 Hz), 2.75 (1H, dd, J=16.5, 7.5 Hz), 3.13 (1H, dddd, J=10.5, 7.5, 7, 5.5 Hz), 4.20 (2H, q, J=7 Hz)

Example 4

Preparation of benzyl 4-cyclopropyl(dimethyl)silyl-3-cyanobutanoate

[Formula 4]

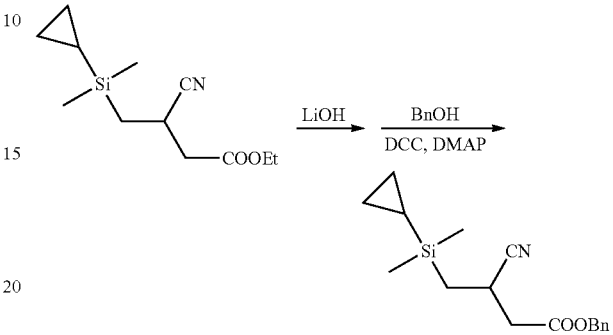

Ethyl 4-cyclopropyl(dimethyl)silyl-3-cyanobutanoate (6.39 g, 26.7 mmol) obtained in Example 3 mentioned above was hydrolyzed by using lithium hydroxide in the same manner as that of the aforementioned examples. The obtained reaction mixture (6.21 g) was dissolved in dichloromethane (85 ml), and the solution was added successively with benzyl alcohol (4.95 ml, 48.1 mmol), dicyclohexylcarbodiimide (8.81 g, 42.8 mmol) and 4-dimethylaminopyridine (163 mg, 1.34 mmol). The mixture was stirred for 30 minutes under ice cooling and for further 17 hours at room temperature. After the reaction vessel was cooled on ice, the reaction mixture was added with aqueous hydrochloric acid (1 N), and the mixture was stirred for 5 minutes, and further stirred for 30 minutes at room temperature. The deposited urea was removed by filtration under reduced pressure, and the filtrate was extracted with chloroform. The organic layer was washed with saturated aqueous sodium hydrogencarbonate, and treated in a conventional manner, and then the residue was purified by silica gel column chromatography [hexane/ethyl acetate (24:1 to 19:1)] to obtain benzyl 4-cyclopropyl(dimethyl)silyl-3-cyanobutanoate (7.50 g, 93%) mentioned in the title as colorless oil.

$^1$H-NMR (CDCl$_3$) δ: −0.39 (1H, dddd, J=9.5, 9.5, 7, 7 Hz), 0.00 (6H, s), 0.16-0.28 (2H, m), 0.55-0.66 (2H, m), 0.88 (1H, dd, J=14.5, 5.5 Hz), 1.04 (1H, dd, J=14.5, 10 Hz), 2.65 (1H, dd, J=16.5, 7 Hz), 2.81 (1H, dd, J=16.5, 7.5 Hz), 3.14 (1H, dddd, J=10, 7.5, 7, 5.5 Hz), 5.17 (2H, s), 7.30-7.41 (5H, m)

Example 5

Preparation of 4-amino-3-[cyclopropyl(dimethyl)silyl]methylbutanoic acid

[Formula 5]

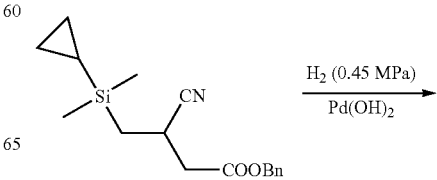

-continued

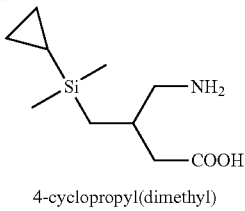

4-cyclopropyl(dimethyl)

Benzyl silyl-3-cyanobutanoate (2.220 g, 7.38 mmol) was subjected to catalytic reduction in methanol in the presence of Pd(OH)$_2$ (hydrogen pressure, 0.45 MPa). After the solvent was evaporated, the residue was recrystallized to obtain 4-amino-3-[cyclopropyl(dimethyl)silyl]methylbutanoic acid (992 mg, 63%) mentioned in the title as colorless fine needle crystals.

Mp: 151.5 to 153° C. (methanol/2-propanol)

$^1$H-NMR (CD$_8$OD) δ: -0.38 (1H, dddd, J=9.5, 9.5, 7, 7 Hz), -0.04 (6H, s), 0.20-0.27 (2H, m), 0.57-0.64 (2H, m), 0.66 (1H, dd, J=15, 6 Hz), 0.73 (1H, dd, J=15, 8 Hz), 2.18-2.30 (1H, m), 2.33 (1H, dd, J=15.5, 9 Hz), 2.54 (1H, dd, J=15.5, 3 Hz), 2.87 (1H, dd, J=12.5, 7.5 Hz), 2.98 (1H, dd, J=12.5, 3.5 Hz)

INDUSTRIAL APPLICABILITY

The compounds represented by the aforementioned general formula (I) and salts thereof provided by the present invention can be used as, for example, an active ingredient of medicament. They have superior stability in vivo, and are useful as an active ingredient of medicaments with a sustained metabolic rate.

What is claimed is:

1. A compound represented by the following formula (I) or a salt thereof:

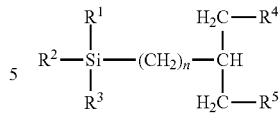

wherein at least one of $R^1$, $R^2$, and $R^3$ represents a cyclic alkyl group, the remaining represents a linear or branched alkyl group;

n represents 0 or 1;

$R^4$ represents an amino group, which amino group may have a substituent, or —(CX$_2$)$_m$—COOH in which m represents an integer of 0 to 3 and X represents a hydrogen atom or a deuterium atom;

$R^5$ represents —(CY$_2$)$_p$—COOR$^6$ in which p represents an integer of 0 to 3, Y represents a hydrogen atom or a deuterium atom, and $R^6$ represents a hydrogen atom or an alkyl group, which alkyl group may have a substituent.

2. The compound or a salt thereof according to claim 1, wherein $R^1$ is cyclopropyl group, $R^2$ and $R^3$ are methyl groups, n is 0 or 1, $R^4$ is an amino group, a monoalkylamino group, or an acylamino group, and $R^5$ is —(CH$_2$)$_p$—COOR$^6$ in which p represents an integer of 0 to 3 and $R^6$ is hydrogen atom or an alkyl group.

3. The compound or a salt thereof according to claim 1, wherein $R^1$ is cyclopropyl group, $R^2$ and $R^3$ are methyl groups, n is 1, $R^4$ is an amino group, and $R^5$ is —(CH$_2$)$_p$—COOR$^6$ in which p represents an integer of 0 to 3 and $R^6$ is a hydrogen atom or an alkyl group.

* * * * *